(12) United States Patent
Kuntze

(10) Patent No.: US 11,009,483 B2
(45) Date of Patent: May 18, 2021

(54) ELECTROCHEMICAL MEASURING CELL FOR MEASURING THE CONTENT OF CHLORINE COMPOUNDS IN WATER

(71) Applicant: Kuntze Instruments GmbH, Meerbusch (DE)

(72) Inventor: Verena Kuntze, Düsseldorf (DE)

(73) Assignee: Kuntze Instruments GmbH, Meerbusch (DE)

( * ) Notice: Subject to any disclaimer, the term of this patent is extended or adjusted under 35 U.S.C. 154(b) by 38 days.

(21) Appl. No.: 15/744,883

(22) PCT Filed: Jul. 11, 2016

(86) PCT No.: PCT/DE2016/100306
§ 371 (c)(1),
(2) Date: Jan. 15, 2018

(87) PCT Pub. No.: WO2017/012607
PCT Pub. Date: Jan. 26, 2017

(65) Prior Publication Data
US 2018/0209934 A1    Jul. 26, 2018

(30) Foreign Application Priority Data

Jul. 22, 2015 (DE) .................... 10 2015 111 849.1

(51) Int. Cl.
*G01N 27/416* (2006.01)
*G01N 27/30* (2006.01)
*G01N 33/18* (2006.01)

(52) U.S. Cl.
CPC ....... *G01N 27/4168* (2013.01); *G01N 27/301* (2013.01); *G01N 27/304* (2013.01); *G01N 33/182* (2013.01)

(58) Field of Classification Search
CPC .... G01N 27/301; G01N 27/304; G01N 27/49; G01N 27/4035; G01N 27/404;
(Continued)

(56) References Cited

U.S. PATENT DOCUMENTS 3,448,032 A * 6/1969 Wise ................... G01N 27/3335
204/417
3,756,923 A * 9/1973 Dahms ............... G01N 27/4045
205/782.5
(Continued)

FOREIGN PATENT DOCUMENTS

DE        195 15 392       11/1996
EP        0 563 690        10/1993
(Continued)

OTHER PUBLICATIONS

Schiavon, Gilberto, Gianni Zotti, Rosanna Toniolo, Gino Bontempelli, Amperometric Monitoring of Sulphur Dioxide in Liquid and Air Samples of Low Conductivity by Electrodes Supported on Ion-exchange Membranes, Analyst, vol. 116, No. 8, p. 797-801 (1991) (Year: 1991).*

(Continued)

*Primary Examiner* — James Lin
*Assistant Examiner* — Vivian A Tran
(74) *Attorney, Agent, or Firm* — Gudrun E. Huckett

(57) ABSTRACT

The invention relates to an electrochemical measuring cell for measuring the content of chlorine compounds in water, having an electrolyte chamber (2) which receives an electrolyte, a measuring electrode (3) which delimits the electrolyte chamber, a reference electrode (5), and a counter-electrode (4). Said electrochemical measuring cell is characterised in that the measuring electrode (3) is a rigid, (Continued)

porous platinum membrane having a pore size of 0.15 μm to 0.25 μm, which produces the contact with the electrolyte and the water.

4 Claims, 1 Drawing Sheet

(58) Field of Classification Search
CPC ........... G01N 27/4045; G01N 27/4168; G01N 33/18; G01N 33/182; G01N 33/004; G01N 33/0049; G01N 27/333; G01N 27/3335
See application file for complete search history.

(56) References Cited

U.S. PATENT DOCUMENTS

| | | | |
|---|---|---|---|
| 3,956,094 A * | 5/1976 | Capuano | G01N 27/4168 204/402 |
| 4,049,382 A * | 9/1977 | Ross, Jr. | G01N 31/00 205/780 |
| 4,552,013 A | 11/1985 | Matson | |
| 4,581,121 A * | 4/1986 | Dailey | G01N 33/1886 204/406 |
| 4,707,242 A | 11/1987 | Schneider et al. | |
| 5,326,449 A | 7/1994 | Cunningham | |
| 5,624,546 A * | 4/1997 | Milco | G01N 27/4045 204/412 |
| 5,725,747 A | 3/1998 | Pinkowski et al. | |
| 5,944,969 A | 8/1999 | Scheffler et al. | |
| 7,790,006 B2 * | 9/2010 | Feng | G01N 27/404 204/415 |
| 2003/0205465 A1 * | 11/2003 | Feng | G01N 27/4045 204/415 |
| 2005/0011771 A1 | 1/2005 | Wittkampf et al. | |
| 2005/0023153 A1 * | 2/2005 | Bakker | G01N 27/3335 205/775 |
| 2005/0029103 A1 * | 2/2005 | Feng | G01N 27/404 204/432 |
| 2006/0163088 A1 * | 7/2006 | Xu | G01N 27/404 205/793 |
| 2015/0177183 A1 * | 6/2015 | Bakker | G01N 27/3335 205/789 |
| 2016/0168732 A1 * | 6/2016 | Swiegers | C25B 15/02 429/500 |

FOREIGN PATENT DOCUMENTS

| | | | |
|---|---|---|---|
| EP | 0563690 A1 * | 10/1993 | ......... G01N 27/4168 |
| EP | 0 740 149 | 10/1996 | |

OTHER PUBLICATIONS

Schiavon G et al.: "Amperometric Monitoring of Sulphur Dioxide in Liquid and Air Samples of Low Conductivity by Electrodes Supported on Ion-Exchange Membrane"; Analyst; London, GB; vol. 116, No. 8; Aug. 1, 1991; pp. 797-801.

Rene Knake et al.: "Amperometric sensing in the gas phase"; Analytica Chimica ACTA, Elsevier, Amsterdam, NL; vol. 549; Jul. 6, 2005; pp. 1-9.

* cited by examiner

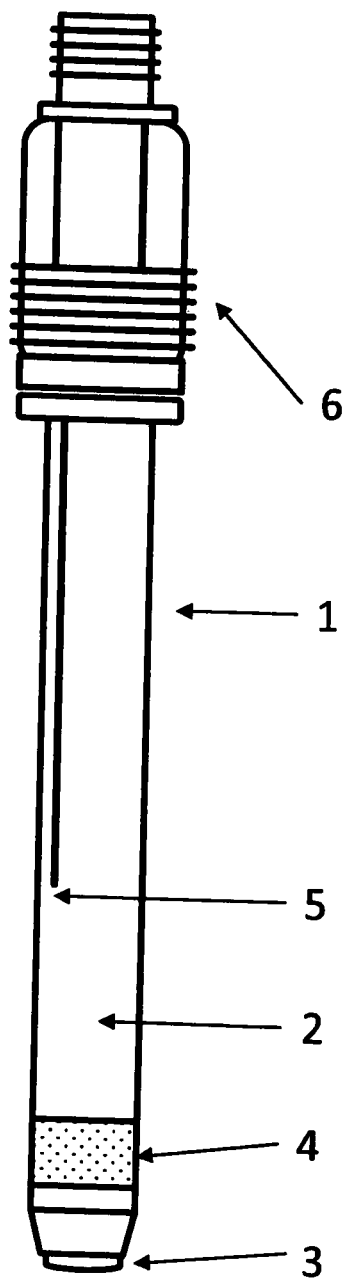

ELECTROCHEMICAL MEASURING CELL FOR MEASURING THE CONTENT OF CHLORINE COMPOUNDS IN WATER

BACKGROUND OF THE INVENTION

The invention concerns an electrochemical measuring cell for measuring the content of chlorine compounds in water, comprising an electrolyte chamber, a measuring electrode delimiting the electrolyte chamber, a counter electrode, and a reference electrode.

Such electrochemical measuring cells are inter alia described in EP 0 740 149 B1, EP 0 563 690 A1, DE 195 15 392 C2, and DE 103 22 894 A1.

These known measuring cells are so-called membrane-covered measuring cells with a hydrophilic, liquid-permeable membrane that delimits the electrolyte chamber or the electrolyte contained therein relative to the liquid to be tested, in particular water.

The known membrane-covered sensors have several disadvantages:

The compounds to be measured must diffuse through the membrane into the electrolyte chamber. This is a slow process, the signal strength drops greatly, and the response time increases greatly in comparison to open electrode systems. Also, a diffusion of the salts dissolved in the electrolyte in opposite direction into the water to be tested can take place; this can significantly shorten the service life of the measuring cell.

Because of the slow diffusion process, the membrane must be as thin as possible. This makes it mechanically delicate. Since the electrolyte due to measurement and storage is used up, it must be changed regularly. For this purpose, a membrane cap must be unscrewed, emptied, rinsed, filled, and again screwed on, wherein also a pressure compensation must be provided for. This handling entails always the risk that the operator in the process will damage the membrane and thereby cause the sensor to become unusable.

Since behind the membrane a material transport is also possible only by diffusion, the spacing between membrane and measuring electrode has a decisive effect on the signal strength. This spacing however can vary due to pressure fluctuations or changes in the inflow so that the measuring signal also displays such pressure or flow changes.

The sensors that are available on the market have very small electrodes with corresponding weak signals which require pre-amplification, i.e., electronics installed in the sensor; this has a negative effect on the manufacturing costs. In order to counteract this, it is not the sensor that is being considered expendable material but only the membrane and the electrolyte. In practice, some manufacturers offer to refurbish, if desired, the electrodes of the sensor for a fee.

Membrane sensors with hydrophilic, liquid-permeable membranes contain different plastic materials, adhesive connections, and seals which react partially sensitive to the ingredients of water, e.g. to surface active agents.

An electrochemical cell disclosed in U.S. Pat. No. 4,707, 242 A contains two working electrodes 20, 22, a reference electrode 34, and a counter electrode 28 and serves for quantitative measurement of harmful gases. The reference electrode 34 and the counter electrode attached to a porous membrane 30 are located in an electrolyte chamber 14 into which the gas to be tested is pumped. The working electrodes 20, 22 according to FIG. 3 are attached as a first unit to a porous gas diffusion membrane 24 forming a second unit. The second working electrode 22 surrounds the first working electrode 20. The first working electrode 20 is produced by mixing a suitable catalyst 40 with a polytetrafluoroethylene dispersion. The catalyst 40 can be comprised of platinum. The second working electrode 22 has a catalytic area 50 which can be comprised of platinum. This known electrochemical cell is not suitable for measuring the chlorine compounds in water.

U.S. Pat. No. 5,326,449 A discloses a sensor for the electrochemical analysis of a catalyzed reagent in solution. This sensor has a composite membrane 140 of a catalytically immobilized protein for conversion of the reagent to be measured into an electrically measurable value. The composite membrane contains a porous membrane 142 of a synthetic polymer material in a thin flexible layer. Into the membrane containing the protein, at least one blocking membrane 148 is partially embedded which is positioned as protective membrane between the porous membrane and the analyte. According to column 7, lines 15ff, the porous membrane elements have a pore size in the range of approximately 0.01 micron to approximately 10 micron, preferably 0.1 to approximately 2 micron. This known sensor is not suitable for measuring the content of chlorine compounds in water.

U.S. Pat. No. 4,552,013 A discloses a liquid chromatography device with a coulometric cell 23 which contains at least one working electrode, at least one reference electrode, and at least one counter electrode. The working electrode 54 contains a material pack 68 of platinum material in powder form with an average grain size between approximately 2 to 3 micron and approximately 400 micron. The material pack 68 is located between two porous membranes or frits of e.g. glass, glass fiber, polypropylene, porous Teflon or the like, and is arranged in a flow channel 46 for the sample solution to be tested which is flowing through the working electrode 54 and thus through the material pack 68 of platinum material in powder form. The cell 23 has no electrolyte chamber. When manufacturing the cell 23, the dry platinum material in powder form is poured onto one of the two porous membranes (frits) and then covered with the second membrane. The purpose of the known cell resides in that disruptive ingredients, for example, oxygen, are to be removed from the sample solution upstream of the chromatography column 28. In U.S. Pat. No. 4,552,013, it is expressed, without a more precise specification, that the known cell can also be used for measuring purposes.

The invention has the object to provide an electromechanical measuring cell for measuring the content of chlorine compounds in water in which it is possible to eliminate a flexible hydrophilic membrane that is as thin as possible in order to avoid the afore described risks or disadvantages when handling and cleaning the measuring cell, without negatively affecting future measuring results.

SUMMARY OF THE INVENTION

This object is solved according to the invention in that the measuring electrode is a rigid porous platinum membrane that produces a contact with the electrolyte and with the water and has a pore size of 0.15 μm to 0.25 μm. The porous platinum membrane that at the same time forms the measuring electrode serves to prevent the water to be tested from entering the electrolyte chamber which receives the electrolyte and to have the reaction take place in the pores of the platinum membrane and to measure the generated reaction products directly as they are generated.

The water to be tested flows past the measuring cell and comes into contact with the electrolyte only within the electrode pores and membrane pores.

The measuring cell according to the invention is one for amperometric, potentiostatic measurement of chlorine compounds.

Preferred embodiments of the invention are disclosed in the dependent claims: the pore size amounts to 0.2 µm; the counter electrode contains platinum; the counter electrode is a platinum ring surrounding the electrolyte chamber; the platinum membrane has a thickness of 0.5 mm+/−0.05 mm.

In the measuring cell according to the invention, the membrane and the measuring electrode are combined in one component. The microporous platinum membrane separates the electrolyte chamber from the water to be tested so that active ingredients of the electrolyte and of the substances to be measured of the water meet in the pores of the measuring electrode, react therein, and the formed reaction product is detected.

Combining the two functions (membrane and measuring electrode) in one component eliminates the prior problems of the pressure effect and of the flow effect and optimizes the diffusion problem. Since a rigid component that is fixedly installed and must not be exchanged is provided, the new measuring cell is mechanically robust and does not entail the risk that the user by faulty exchange of expendable parts will endanger the measurement.

Since the electrolyte is in contact with the water only through the rigid platinum membrane, washing out the electrolyte is substantially precluded.

The contact surface area electrolyte/water in the porous membrane is multiple times greater than in conventional membrane sensors, the obtained signal is strong and requires no pre-amplification. The measuring cell can therefore be constructed in the form of the 12 mm glass sensors that are conventional for water-analytical measuring cells and can be installed by means of its typical PG13.5 thread in typical pH instruments or redox instruments.

The measuring cell is manufactured of glass and therefore insensitive relative to most ingredients of water, such as e.g. surface active agents.

The combined embodiment of membrane and measuring electrode in the form of a porous platinum has the advantage that the measuring cell remains clean and active for a long period of time. The measuring cell according to the invention can be used without problems in applications in which no disinfecting agent is present for extended periods of time.

Platinum electrodes are used, for example, in fuel cells. In this context, only the surface enlargement is utilized in order to lower material costs. The known platinum electrodes also do not serve in particular for amperometric measurement but only for substance conversion.

Porous platinum electrodes that are used for measurement and in which substances pass through the membrane pores are found, for example, in lambda sensors that are used for regulating the air supply in exhaust gas catalysts. In this context, this however does not concern amperometric measurements but redox measurements.

BRIEF DESCRIPTION OF THE DRAWING

FIG. 1 shows a measuring cell according to the invention.

DESCRIPTION OF PREFERRED EMBODIMENT

The measuring cell is comprised according to the drawing of a 12 mm glass housing 1 having attached at its bottom end the measuring electrode 3 in the form of a rigid microporous platinum membrane with a pore size of 0.15 µm to 0.25 µm, preferably 0.2 µm. In the interior of the housing 1, there is the reference electrode 5 and the electrolyte chamber 2. In the shaft-like housing 1, a platinum ring as a counter electrode 4 is attached. At the top end of the housing, there is a connecting head 6 for connecting to a measured value evaluation unit.

The porous platinum membrane of the measuring electrode 3 leads to an intimate contact between the electrolyte and the substance to be measured in the pores of the platinum membrane 3. The resulting product is detected at the measuring electrode 3 and reduced in this context. This leads to a current flow that is proportional to the concentration of the substance to be measured.

What is claimed is:

1. An electrochemical measuring cell for measuring the content of chlorine compounds in water, the electrochemical measuring cell comprising:
   an electrolyte chamber comprising an electrolyte arranged in an interior of the electrolyte chamber;
   a measuring electrode delimiting the electrolyte chamber;
   a reference electrode arranged in the electrolyte in the interior of the electrolyte chamber;
   a counter electrode arranged outside of the electrolyte chamber;
   wherein the measuring electrode is a rigid membrane consisting of porous platinum having a pore size of 0.15 µm to 0.25 µm, wherein the rigid membrane consisting of porous platinum has a thickness of 0.5 mm+/−0.05 mm, wherein the rigid membrane consisting of porous platinum comprises a first face facing the electrolyte and exposed to the electrolyte and further comprises a second face opposite to the first face, wherein the second face faces away from the electrolyte and is exposed to the water to be tested, wherein within the rigid membrane consisting of porous platinum a physical and an electrical contact between the water to be tested and the electrolyte is taking place.

2. The electrochemical measuring cell according to claim 1, wherein the pore size amounts to 0.2 µm.

3. The electrochemical measuring cell according to claim 1, wherein the counter electrode contains platinum.

4. The electrochemical measuring cell according to claim 1, wherein the counter electrode is a platinum ring surrounding the electrolyte chamber.

* * * * *